US012226396B2

(12) United States Patent
Ellervik et al.

(10) Patent No.: US 12,226,396 B2
(45) Date of Patent: Feb. 18, 2025

(54) GLUCONIC ACID DERIVATIVES FOR USE IN THE TREATMENT AND/OR PREVENTION OF MICROBIAL INFECTIONS

(71) Applicant: GEDEA BIOTECH AB, Lund (SE)

(72) Inventors: Ulf Ellervik, Löddeköpinge (SE); Olov Sterner, Malmö (SE); Helena Strevens, Lund (SE); Sophie Manner, Helsingborg (SE)

(73) Assignee: Gedea Biotech AB, Lund (SE)

( * ) Notice: Subject to any disclaimer, the term of this patent is extended or adjusted under 35 U.S.C. 154(b) by 0 days.

(21) Appl. No.: 18/163,321

(22) Filed: Feb. 2, 2023

(65) Prior Publication Data

US 2023/0181523 A1  Jun. 15, 2023

Related U.S. Application Data

(62) Division of application No. 16/753,899, filed as application No. PCT/EP2018/077129 on Oct. 5, 2018, now Pat. No. 11,612,584.

(30) Foreign Application Priority Data

Oct. 6, 2017 (EP) .................................... 17195192

(51) Int. Cl.
| | |
|---|---|
| *A61K 31/366* | (2006.01) |
| *A61K 9/00* | (2006.01) |
| *A61K 31/191* | (2006.01) |
| *A61K 31/765* | (2006.01) |
| *A61K 45/06* | (2006.01) |
| *A61P 31/04* | (2006.01) |

(52) U.S. Cl.
CPC .......... *A61K 31/366* (2013.01); *A61K 31/191* (2013.01); *A61K 31/765* (2013.01); *A61P 31/04* (2018.01); *A61K 9/0034* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 6,361,789 B1 | 3/2002 | Zuccato et al. | |
| 7,569,530 B1 | 8/2009 | Pan et al. | |
| 8,795,693 B2 | 8/2014 | Tamarkin et al. | |
| 9,101,662 B2 | 8/2015 | Tamarkin et al. | |
| 10,993,907 B2 * | 5/2021 | Ellervik | A61K 31/496 |
| 11,026,883 B2 | 6/2021 | Masto et al. | |
| 11,696,891 B2 * | 7/2023 | Ellervik | A61K 31/513 |
| | | | 424/432 |
| 2004/0126369 A1 | 7/2004 | Payne et al. | |
| 2006/0105008 A1 | 5/2006 | Ahmad | |
| 2006/0172007 A1 * | 8/2006 | Ahmad | A61K 9/0034 |
| | | | 514/557 |
| 2007/0059278 A1 | 3/2007 | Ahmad et al. | |
| 2008/0058421 A1 | 3/2008 | Lopes | |

FOREIGN PATENT DOCUMENTS

| | | |
|---|---|---|
| AU | 2012250862 B2 | 11/2012 |
| CN | 101305993 A | 11/2008 |
| CN | 102070774 A | 5/2011 |
| EP | 1764100 | 3/2007 |
| JP | 2002138142 A | 5/2002 |
| JP | 2007-0771450 | 3/2007 |
| JP | 2017-501741 | 1/2017 |
| KR | 101841976 B1 | 5/2018 |
| WO | WO2000/44230 A1 | 8/2000 |
| WO | WO2002/087570 A1 | 11/2002 |
| WO | WO2004/000016 A2 | 12/2003 |
| WO | WO2005/105070 A2 | 11/2005 |
| WO | 2008108834 A2 | 9/2008 |
| WO | 2010129443 A2 | 11/2010 |
| WO | 2016141946 A1 | 9/2016 |
| WO | 2017174731 A1 | 10/2017 |
| WO | WO2019/068862 A1 | 4/2019 |
| WO | WO2020/201515 A1 | 10/2020 |

OTHER PUBLICATIONS

Marion Owen, Management of Vaginitis, Dec. 1, 2004, American Family Physician, vol. 70 (Year: 2004).*
Mayo Clinic Staff, Preterm Labor, Feb. 8, 2022, Mayo Clinic (Year: 2022).*
Roberts et al. Treatment of asymptomatic vaginal candidiasis in pregnancy to prevent preterm birth: an open label pilot randomized controlled trial, BMC Pregnancy and Childbirth 2011, 11:18 (Year: 2011).*
New Food Industry, 47(3): 45-54, 2005.
Nieto-Penalver, C. et al., Gluconic acid produced by Gluconacetobacter diazotrophocus Pal5 possesses antimicrobial properties, Research in Microbiology, 165: 549-558, 2014.
English Translation of Japanese Reasons for Rejection, Japanese Application No. 2020-519028, Oct. 11, 2022.
Dujon, B. et al., Genome evolution in yeasts, Nature, Year:2004, 430, (35-44).
Gillum, A.M. et al., Isolation of the Candida Albicans Gene for orotidine-5'-phosphate Decarboxylase by Complementation of S. Cerevisiae ura3 and E. coli purF Mutations, Mol. Gen. Genet, Year: 1984, 198, (179-182).
Moyes, D.L. et al., Candidalysin is a fungal peptide toxin critical for mucosal infection, Nature, Year: 2016, 532, (64-68).
Sawyer, D. et al., The Lactone-Acid-Salt Equilibria for D-Glucono-do-lactone adn the Hydrolysis Kinetics for this Lactone, J. Am. Chem. Soc., Year: 1959, 81, (5302-5306).

(Continued)

*Primary Examiner* — Abigail Vanhorn
*Assistant Examiner* — Ali S Saeed
(74) *Attorney, Agent, or Firm* — Weston R. Gould; Dinsmore & Shohl LLP

(57) ABSTRACT

Pharmaceutical compositions and methods of using said pharmaceutical compositions are provided herein. A method of preventing preterm birth in a pregnant individual is also provided, said method comprising administering to said individual a pharmaceutical composition comprising a compound of Formula XX or a lactone thereof of formula XIX or XXI and preventing said preterm birth by said administration.

13 Claims, 10 Drawing Sheets

(56) References Cited

OTHER PUBLICATIONS

Scherz, K. et al., Genetic Basisc for *Saccharomyces cerevisiae* Biofilm in Liquid Medium, G3 (Bethesda), Year: 2014, 4, (1671-1680).

Serrano-Fujarte, I. et al., Influence of Culture Media on Biofilm Formation by *Candida* Species and Response of Sessile Cells to Anitfungals and Oxidative Stress, Biomed Res Intl., Year: 2015; 2015:783639.

* cited by examiner

A

B

A

B

A

B

A

B

GLUCONIC ACID DERIVATIVES FOR USE IN THE TREATMENT AND/OR PREVENTION OF MICROBIAL INFECTIONS

CROSS REFERENCE TO RELATED APPLICATIONS

This application is a divisional of U.S. patent application Ser. No. 16/753,899, filed Apr. 6, 2020, which is a U.S. National Stage of international application PCT/EP2018/077129 filed Oct. 5, 2018, which claims priority to European Application No: 17195192.4 filed Oct. 6, 2017, the entire contents of each of which are incorporated herein by reference.

TECHNICAL FIELD

The present invention relates to a compound of Formula I for use in the treatment and/or prevention of microbial infections. Furthermore, the present invention relates to a method for prevention and/or reduction of biofilm formation.

BACKGROUND

Antimicrobial agents have been used for the last 70 years to treat patients who have infectious diseases. Since the 1940s, these drugs have greatly reduced illness and death from infectious diseases. However, these drugs have been used so widely, and for so long, that the infectious organisms the antimicrobial agents are designed to kill have adapted to them. As a result, the medicines become ineffective and infections persist in the body, increasing the risk of spread to others.

Antimicrobial resistance threatens the effective prevention and treatment of an ever-increasing range of infections caused by bacteria, parasites, viruses and fungi.

Thus, antimicrobial resistance is an increasingly serious threat to global public health that requires action across all government sectors and society.

All classes of microbes develop resistance: fungi develop antifungal resistance, viruses develop antiviral resistance, protozoa develop antiprotozoal resistance, and bacteria develop antibiotic resistance.

The problem with antibiotic resistance is a common phenomenon. Fungal infections that are resistant to treatment are an emerging public health problem. Overall, antifungal resistance is still relatively uncommon, but the problem will likely continue to evolve unless more is done to prevent further resistance from developing and prevent the spread of these infections. Although most antifungal resistance occurs in *Candida* species, resistance in other types of fungi, such as *Aspergillus*, is also an emerging issue.

Since fungi are eukaryotes, just like the human hosts they infect, there are only few distinct targets that can be employed for antifungal drug development. Hence antifungals are mostly restricted to drugs targeting a few metabolic pathways.

One target for antimicrobial agents is the biofilm which is a product of a microbial developmental process. Biofilms are formed by microbial cells stuck to each other and surrounded by the self-produced extracellular polymeric matrix. Formation of biofilm is a survival strategy for bacteria and fungi to adapt to their living environment, especially in a hostile environment. When a cell switches to the biofilm mode of growth, it undergoes a phenotypic shift in behaviour in which large suites of genes are differentially regulated. Biofilms can contain many different types of microorganism, e.g. bacteria, archaea, protozoa, fungi and algae.

Biofilms are estimated to be associated with 80% of microbial infections and growth of micro-organisms in biofilms may enhance their resistance to antimicrobial agents. In addition, biofilm bacteria are up to 1000-fold more tolerant and/or resistant to antibiotics than planktonic cells.

In most fungi, hyphae are the main mode of vegetative growth, and are collectively called a mycelium. For example, the virulence of *Candida albicans* is mediated by a transformation from planktonic cells into hyphae. The hyphal form, i.e. filamentous cells, has the ability to invade tissue and induce inflammation, mediated by candidalysin, a cytotoxic peptide toxin that destroys the epithelial cells (Moyes et. al., Nature, 2016, 532, 64).

Antimicrobial resistance is not only problematic in primary infections, but also in secondary infections. Without effective antimicrobials for prevention and treatment of infections, medical procedures such as organ transplantation, cancer chemotherapy, diabetes management and major surgery become very high risk. Furthermore, fungal infections have become one of the major causes of morbidity and mortality in immunocompromised patients, such as those with HIV/AIDS, tuberculosis or receiving chemotherapy. Despite increased awareness and improved treatment strategies, the frequent development of resistance to the antifungal drugs used in clinical settings contributes to the increasing toll of mycoses.

Thus, there is an emerging need for novel antimicrobial agents.

SUMMARY

The present disclosure concerns a compound of Formula I for use in preventing preterm birth. The present disclosure shows that treatment with a compound of Formula I,

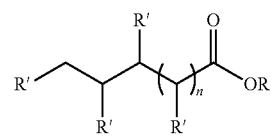

or a lactone thereof, wherein

R is selected from the group consisting of —H, -alkyl, —C(O)alkyl and phenyl;

R' is independently selected from the group consisting of —OR, —H and halogen; and n is an integer 1, 2 or 3;

reduces the presence of biofilm of fungi species, and to have a cytotoxic effect on several fungi species. Furthermore, the present disclosure shows that a compound of formula I is useful at preventing pre-term birth.

Thus, in one aspect, the present disclosure concerns a method for preventing preterm birth in a pregnant individual, said method comprising administering to said individual a pharmaceutical composition comprising a compound of Formula XX,

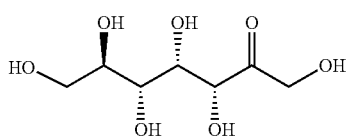

or a lactone thereof of formula XIX or XXI,

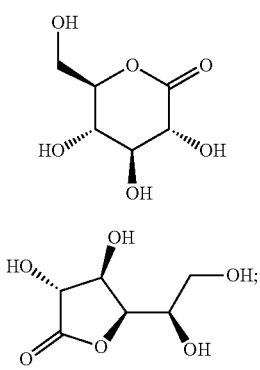

and
preventing said preterm birth by said administration.

In some embodiments, the compound is of Formula XIX or Formula XX. In some embodiments, the compound is of Formula XIX. In some embodiments, the pharmaceutical composition comprises the compound of Formula XIX and the compound of Formula XX. In some embodiments, the pharmaceutical composition comprises at least 5 wt % of the compound of Formula XX, XIX or XXI. In some embodiments, the pharmaceutical composition comprises no more than 10 wt % water.

In some embodiments, the compound of Formula XX, XIX or XXI is the sole antimicrobial agent in said pharmaceutical composition. In some embodiments, the pharmaceutical composition consists of the compound of Formula XIX alone or in combination with the compound of Formula XX or the compound of Formula XXI, or both, and one or more pharmaceutically acceptable excipients.

In some embodiments, the individual is a mammal, optionally a human. In some embodiments, said individual has an elevated risk for preterm birth. In some embodiments, the pharmaceutical composition is administered vaginally, optionally by being formulated as a tampon, vagitorium, vaginal aerosol, vaginal cup, vaginal gel, vaginal insert, vaginal patch, vaginal ring, vaginal sponge, vaginal suppository, vaginal cream, vaginal emulsion, vaginal foam, vaginal lotion, vaginal ointment, vaginal powder, vaginal shampoo, vaginal solution, vaginal spray, vaginal suspension, vaginal tablet, vaginal rod, vaginal disc, vaginal device, and any combination thereof, or wherein the pharmaceutical composition is present on a sanitary article.

In some embodiments, said composition is administered as an oligomer or polymer, optionally comprising one or more compounds selected from the group consisting of gluconic acid and δ-gluconolactone. In some embodiments, the oligomer or polymer further comprises lactic acid.

DETAILED DESCRIPTION

Compounds

Figure 1:
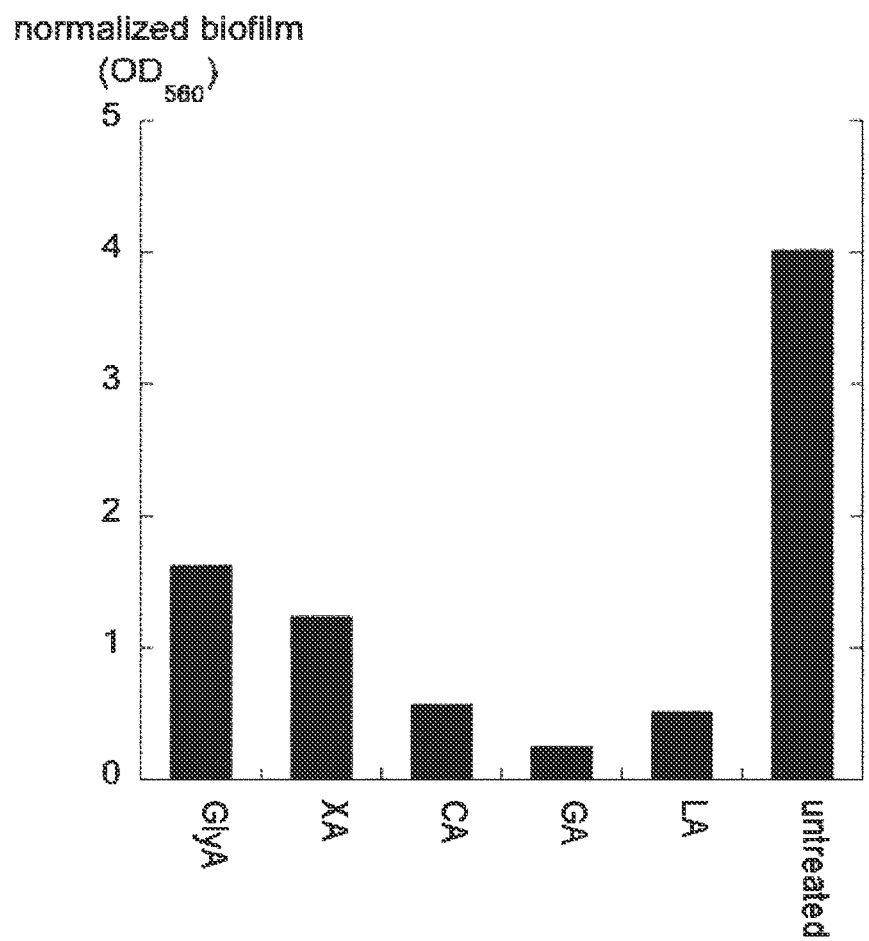
FIG. 1. Normalized biofilm formation of Candida albicans treated with different acids. GlyA=glyceric acid (pH=7), XA=xylonic acid (pH=7), CA=citric acid (pH=4.6), GA=gluconic acid (pH=6.5), LA=lactic acid (pH=4.9), The biofilm was measured after 24 h.

In one aspect, the present invention concerns a pharmaceutical composition comprising a compound of Formula I,

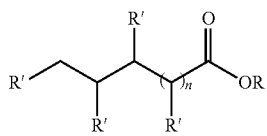

or a lactone thereof, wherein
R is selected from the group consisting of —H, -alkyl, —C(O)alkyl and phenyl;
R' is independently selected from the group consisting of —OR, —H and halogen; and
n is an integer 1, 2 or 3,
for use in the treatment and/or prevention of microbial infections, with the proviso that if the microbial infection is a fungal infection, then the compound of Formula I is not a compound of Formula (XIV)

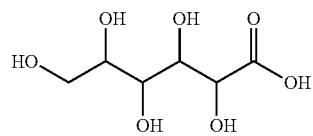

or a lactone thereof.

In one embodiment, the alkyl is a $C_1$ to $C_{20}$ aliphatic chain. The term "aliphatic chain" as used herein refers to non-aromatic hydrocarbons. Said aliphatic chains may be linear, branched and/or cyclic. Said aliphatic chains may be saturated or unsaturated. In said aliphatic chains, one or more hydrogens may be substituted by an aromatic moiety, comprising one or more benzene moieties In one embodiment, the alkyl is a $C_1$ to $C_{20}$ aliphatic chain wherein one or more hydrogens is optionally substituted for —OH, =O, or phenyl, and wherein one or more of the $CH_2$-groups of the aliphatic chain is optionally substituted for O, S, or NH. Non-limiting examples of alkyls where one or more of the $CH_2$-groups of the aliphatic chain is optionally substituted for O, S, or NH are ethers, thioethers and tertiary amines. In one embodiment, alkyl is a $C_1$ to $C_{20}$ aliphatic chain, such as a $C_1$ to $C_{15}$ aliphatic chain, $C_1$ to $C_{10}$ aliphatic chain, $C_1$ to C5 aliphatic chain, such as a C5 to C20 aliphatic chain, such as a $C_5$ to $C_{15}$ aliphatic chain, such as a $C_5$ to $C_{10}$ aliphatic chain, such as a $C_{10}$ to $C_{20}$ aliphatic chain, such as a $C_{10}$ to $C_{15}$ aliphatic chain. In a preferred embodiment, alkyl is selected from the group consisting of methyl, ethyl, and propyl.

In one embodiment, at least one of R' is —OR. In one embodiment, at least two, such as at least three, such as at least four, such as at least five, such as at least six of R' is OR. In a preferred embodiment, R' is —OR.

In one embodiment, at least one of R' is —OH. In another embodiment, no more than one of R' is —H, such as no more than two of R' is —H. In a preferred embodiment, R is —H.

In one embodiment, —OR is acetate or lactate.

In aqueous solution, compounds according to Formula I may be in equilibrium with corresponding lactones, e.g. δ-lactone and γ-lactone. In one embodiment, the compound of Formula I is a lactone thereof. Said lactone may preferably be a δ-lactone or a γ-lactone.

In one embodiment, the compound of Formula I is selected from the group consisting of

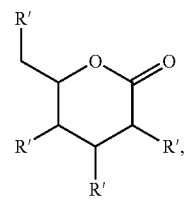

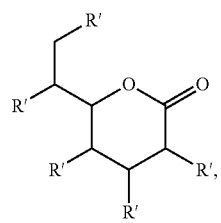

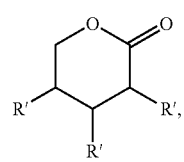

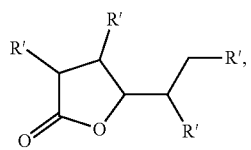

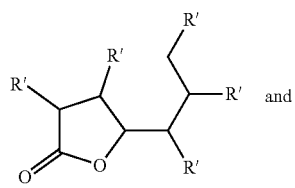

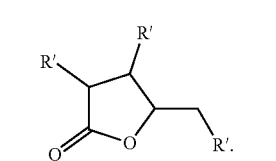

In another embodiment, the compound of Formula I is selected from the group consisting of

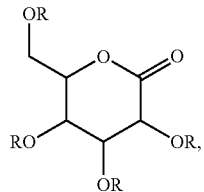

VIII

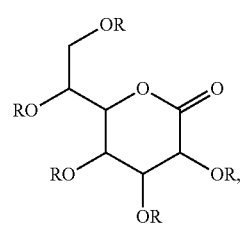

IX

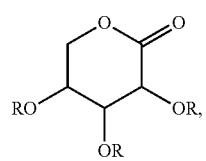

X

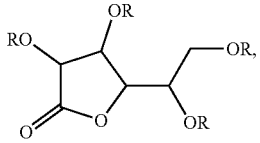

XI

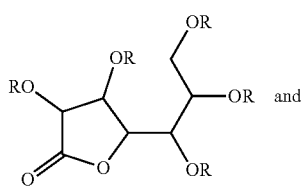

XII

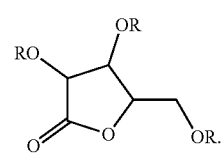

XIII

In a preferred embodiment, n is 2.
In one embodiment, the compound of Formula I is

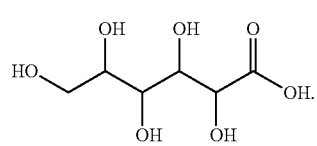

XIV

In one embodiment, the compound of Formula I is a compound of Formula XV,

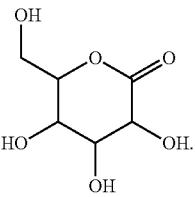

XV

In one embodiment, the compound of Formula I is selected from the group consisting of

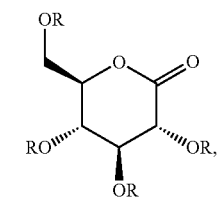

XVI

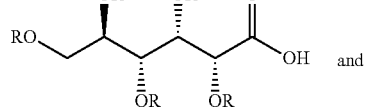

XVII

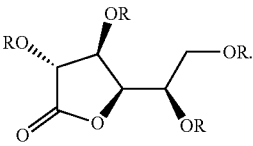

XVIII

In one embodiment, the compound of Formula I is selected from the group consisting of

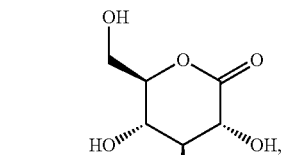

XIX

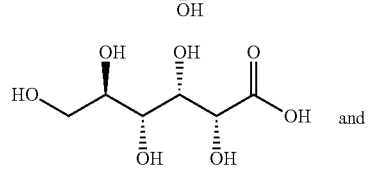

XX

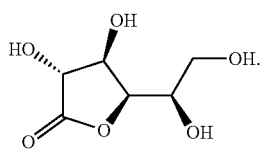

XXI

In one embodiment, compounds XIX, XX and XXI are in equilibrium in aqueous solution.

In a preferred embodiment, the compound of Formula I is glucono-δ-lactone (GDA, Formula XIX),

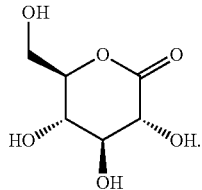

XIX

In another embodiment, the compound is not glucono-δ-lactone (Formula XIX). Thus, in one aspect, the present invention concerns a compound of Formula I for use in the treatment and/or prevention of microbial infections, with the proviso that the compound of Formula I is not glucono-δ-lactone (Formula XIX).

In one embodiment, the present invention concerns a compound of Formula I for use in the treatment and/or prevention of microbial infections, with the proviso that if the compound of Formula I is the compound of Formula XIX, then the microbial infection is not a fungal infection.

In one embodiment, the present invention concerns a compound of Formula I for use in the treatment and/or prevention of microbial infections, with the proviso that if the compound of Formula I is the compound of Formula XIX, then the microbial infection is not a urogenital fungal infection.

In one embodiment, the present invention concerns a compound of Formula I for use in the treatment and/or prevention of microbial infections, with the proviso that if the compound of Formula I is the compound of Formula XIX, then the microbial infection is not vulvovaginal candidosis.

In one embodiment, the present invention concerns a compound of Formula I for use in the treatment and/or prevention of microbial infections, with the proviso that if the microbial infection is a urogenital fungal infection, then the compound of Formula I is not a compound of Formula XIV.

In one embodiment, the compound is an acetal of a compound of Formula I. In one embodiment, the oxo group of the compound is a corresponding acetal, i.e. the compound of Formula I is selected from the group consisting of

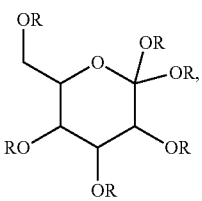

XXII

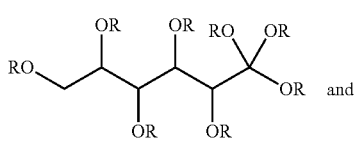

XXIII

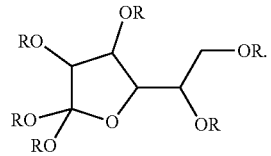

XXIV

In one embodiment, the compound of Formula I is selected from the group consisting of

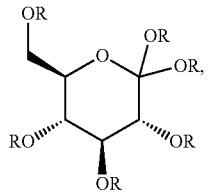

XXV

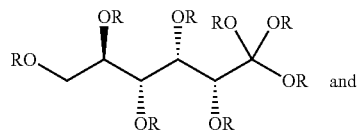

XXVI and

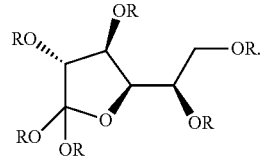

XXVII

Polymer/Oligomer

In one embodiment, the compound of Formula I is oligomerized to form an oligomer. In another embodiment, the compound of Formula I is polymerized to form a polymer.

In one embodiment, the oligomer or polymer comprises one compound of Formula I, i.e. is a homo-oligomer/polymer wherein one compound of Formula I is the monomer.

In another embodiment, the oligomer or polymer is a mixed oligomer/polymer, i.e. a hetero-oligomer/polymer. In one embodiment, the oligomer comprises at least two different compounds of Formula I.

In one embodiment, the oligomer or polymer further comprises lactic acid, i.e. is a lactic acid oligomer/polymer.

In one embodiment, two compounds of Formula I are linked to form a dimer. In one embodiment, the dimer comprises two compounds of Formula XIV. In one embodiment, the dimer comprises two different compounds of Formula I.

Infections

In one aspect, the present invention concerns a compound of Formula I or a pharmaceutical composition comprising a compound of Formula I for use in the treatment and/or prevention of microbial infections. In one embodiment, the present invention relates to glucono-δ-lactone for use in the treatment of a bacterial infection or a mixed fungal and bacterial infection.

In one embodiment, the microbial infection is a urogenital infection. In one embodiment, the microbial infection is a vaginal infection.

In one embodiment, the infection is an infection in a mammal, i.e. the subject in need of said treatment is a mammal. Preferably, the mammal is a human. In one embodiment, the human is a woman. Said woman may be a woman who is pregnant.

In one embodiment, the infection is dermatitis and/or eczema. Said dermatitis and/or eczema may be Seborrhoeic dermatitis. The infection may also be a secondary infection of said dermatitis or eczema.

The term "secondary infection" as used herein refers to a sequela or complication of a root cause. Said root cause may be a primary infection.

In one embodiment, the infection is acne of all severities, or acneiform conditions such as rosacea, perioral or periorbital dermatitis.

In one embodiment, the infection is furunculosis, carbunculosis or folliculitis.

In one embodiment, the infection is cheilitis. Said cheilitis may be angular cheilitis.

In one embodiment, the infection is an infection of the face, scalp, torso and/or groin. The infection may be an infection of infected skin wounds in said areas. The infection may also be located in skinfolds of the body.

In one embodiment the infection is impetigo or erysipelas.

In one embodiment, the infection is an infection of the feet. Said infection of the feet may be associated with diabetic foot wounds. In one embodiment, the infection of the feet is secondary to ingrown toenails or blisters of the feet.

In one embodiment, the infection is a secondary infection arising after an animal bite. Said animal may be an insect. In one embodiment, the infection is a secondary infection arising after insect bites, mosquito bites, tic bites, erythema migrans or lymphadenosis benigna cutis.

In one embodiment, the infection is a secondary infection of herpes simplex, dermatological, oral or genital, or a secondary infection of herpes zoster or varicella zoster.

In one embodiment, the infection is a secondary infection of injury to the skin, such as burns or cuts.

In one embodiment, the infection is a fungal, bacterial or mixed blepharitis.

In one embodiment, the infection is conjunctivitis.

In one embodiment, the infection is a vaginitis or a cervicitis.

In one embodiment, the infection is caused by *Trichomonas vaginalis*. In one embodiment, the infection is trichomoniasis.

In one embodiment, the microbial infection is selected from the group consisting of fungal infections, bacterial infections and mixed fungal and bacterial infections.

Bacterial Infections

In some embodiments, the microbial infection is a bacterial infection. In one embodiment, the microbial infection is a mixed fungal and bacterial infection.

In one embodiment, the bacterial infection is periodontitis.

In one embodiment, the bacterial infection is bacterial vaginosis.

In one embodiment, the bacterial infection is selected from the group consisting of

*Gardnerella vaginalis*-, *Chlamydia trachomatis*-, *Neisseria gonorrhoeae*-, *Treponema pallidum* (syphilis)-, *Atopobium vaginae*-, *Prevotella* spp-, *Mobiluncus* spp-, *Peptostreptococcus* spp-, Poryphyromonas spp-, *Mycoplasma hominis*-, *Bacteroides* spp-, *Ureaplasma urealyticum*-, *Streptococcus* spp-, Enterobacteriaceae-, Enterococci-, *Staphylococcus* spp-, *Propionibacterium*-, *Escherichia coli*-, *Klebsiella*-, *Staphylococcus epidermidis*-, *Staphylococcus aureus*-, *Pseudomonas aeruginosa*-, *Acetinobacter baumanii*-, *Streptococcus pyogenes*-, *Streptococcus agalactiae*-, Beta-Hemolytic Streptococci Groups C and G- and/or *Porphyromonas gingivalis* infection.

In one embodiment, the infection is secondary to oral, nasal or anogential colonization of group A or group B streptococci or multiresistant bacteria.

In one embodiment, the infection is perianal streptococcal dermatitis.

Mixed Fungal and Bacterial Infections

In one embodiment, said microbial infection is a mixed fungal and bacterial infection. The bacterial component of said mixed fungal and bacterial infection may be as the bacterial infection as defined herein. The fungal component of said mixed fungal and bacterial infection may be as the fungal infection as defined herein. In one embodiment, said fungal component of the mixed fungal and bacterial infection is a candidiasis.

Said mixed fungal and bacterial infection may be intertriginous dermatitis or paronychia.

Fungal Infections

In some embodiments, the microbial infection is a fungal infection. In one embodiment, the microbial infection is a mixed bacterial and fungal infection. In one embodiment, said fungal infection is a mycosis. Said mycosis may be selected from the group consisting of Dermatophytosis, Candidiasis, Coccidioidomycosis, Histoplasmosis, Blastomycosis, Paracoccidioidomycosis, Sporotrichosis, Chromomycosis and phaeomycotic abscess, Aspergillosis, Cryptococcosis, Zygomycosis, and Mycetoma.

In a preferred embodiment, the mycosis is Candidiasis. Said Candidiasis may be selected from the group consisting of Candidiasis of vulva and vagina; Candidiasis of skin and nail; Candidiasis of urogenital and gastrointestinal sites; Candidal stomatitis; *Candida* of the breast and nipple; Pulmonary candidiasis; Candidal meningitis; Candidal endocarditis; and Candidal sepsis.

In one embodiment, the mycosis is Dermatophytosis. Said Dermatophytosis may be selected from the group consisting of *Tinea unguium*; toenail onychomycosis; *Tinea inguinalis, Tinea pedis; Tinea* manuum; Tinae *barbae, Tinea amiantacea Tinea capitis; Tinea corporis; Tinea imbricata*; and *Tinea cruris.*

In one embodiment, the fungal infection is selected from the group consisting of *Candida* species infections, such as *Candida albicans*-, *Candida krusei*-, *Candida glabrata*-, *Candida tropicalis* infections; *Trichophyton* species infections, such as *Trichophyton verrucosum*-, *Trichophyton rubrum*-, *Trichophyton violaceum*-, *Trichophyton tonsurans*-; and *Microsporum* species infections, such as *Microsporum canis* infection; *Aspergillus* infections and *Malassezia* infections.

In one embodiment, the infection is caused by *Saccharomyces cerevisiae.*

In one embodiment, the mycosis is *Pityriasis versicolor.*

In one embodiment, the compound of Formula I is not the compound of Formula XIX and the fungal infection is not a urogenital fungal infection.

In another embodiment, the compound of Formula I is not the compound of Formula XIX and the fungal infection is not vulvovaginal candidosis.

In yet another embodiment, the fungal infection is not a urogenital fungal infection and the compound of Formula I is not

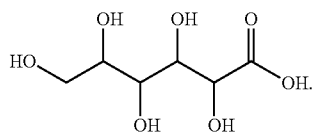

XIV

Viral Infections

In one embodiment, the microbial infection is a viral infection. In one embodiment, the viral infection is HIV.

Formulations

In some embodiments, the present invention relates to a pharmaceutical composition comprising a compound of formula I for use in the treatment of a microbial infection. In one embodiment, the pharmaceutical composition is formulated as a tablet, orally disintegrating tablet (or orally dissolving tablet (ODT)), lozenge, gum, chewing gum, cream, lotion, gel, emulsion, solution, foam, ointment, spray, suspension mouthwash, mouth rinse, oral rinse, mouth bath, nail polish, dermal patch or shampoo. In one embodiment, said solution as adapted for use in a bandage, dressing and/or compress.

In one embodiment, the pharmaceutical composition comprises at least 5 wt %, such as at least 10 wt %, such as at least 15 wt %, such as at least 20 wt %, such as at least 25 wt %, such as at least 30 wt %, such as at least 40 wt %, such as at least 50 wt %, such as at least 60 wt % of the compound of Formula (I).

In one embodiment, the pharmaceutical composition for use according to any one of the preceding claims, wherein the pharmaceutical composition comprises no more than 99 wt %, such as no more than 95 wt %, such as no more than 90 wt %, such as no more than 85 wt %, such as no more than 80 wt %, such as no more than 75 wt % of the compound of Formula (I).

In one embodiment, the pharmaceutical composition comprises 5 to 99 wt %, such as in 10 to 95 wt %, such as in 15 to 95 wt %, such as in 20 to 90 wt %, such as in 40 to 95 wt %, such as in 40 to 95 wt %, such as in 50 to 95 wt % of the compound of Formula (I).

In one embodiment, the pharmaceutical composition comprises no more than 10 wt % water, such as no more than 5 wt % water.

An "antimicrobial agent", as used herein, refers to an agent that is capable of decreasing or eliminating or inhibiting the growth of microorganisms such as that term is known in the art (exemplary microorganisms include microbes such as bacteria, fungi, viruses and other pathogens). Similarly, the term "antifungal agent" refers to an agent that is capable of decreasing or eliminating or inhibiting the growth of fungi, and the term "antibacterial agent" refers to an agent that is capable of decreasing or eliminating or inhibiting the growth of bacteria.

In one embodiment, the pharmaceutical composition further comprises one or more antifungal agents. In one embodiment, the present invention relates to a method of treatment of one or more microbial infections comprising co-administration of a compound of Formula I and an antimicrobial agent to an individual in need thereof. In one embodiment, said antimicrobial agent is an antifungal agent or an antibacterial agent. Said antifungal agent may be selected form the group consisting of miconazole, terconazole, isoconazole, fenticonazole, fluconazole, nystatin, ketoconazole, clotrimazole, butoconazole, econazole, tioconazole, itraconazole, 5-fluoracil, and metronidazole.

In one embodiment, the pharmaceutical composition further comprises one or more antibacterial agents. Antibiotics are a type of antimicrobial agents used in the treatment and prevention of bacterial infections. Said antibacterial agent may be selected from the group consisting of clindamycin, tetracycline, amoxicillin, ampicillin, erythromycin, doxycycline, lumefloxacin, norfloxacin, afloxam, ciproflaxin, azitromycin, and cefltoxine.

In one embodiment, the pharmaceutical composition further comprises a steroid. Said steroid may be cortisone.

In one embodiment, the pharmaceutical composition is formulated as a tampon, vagitorium, vaginal aerosol, vaginal cup, vaginal gel, vaginal insert, vaginal patch, vaginal ring, vaginal sponge, vaginal suppository, vaginal cream, vaginal emulsion, vaginal foam, vaginal lotion, vaginal ointment, vaginal powder, vaginal shampoo, vaginal solution, vaginal spray, vaginal suspension, vaginal tablet, vaginal rod, vaginal disc, vaginal device, and any combination thereof, or wherein the pharmaceutical composition is present on a sanitary article, such as a tampon, a sanitary napkin, an incontinence pad or diaper, or a panty liner.

In one embodiment, the pharmaceutical composition is adapted for administration at least once daily, such as at least twice daily, such as at least three times daily.

In one embodiment, the pharmaceutical composition is adapted for administration no more than every second day, such as no more than every third day, such as no more than once a week.

In one embodiment, the pharmaceutical composition is adapted for administration for no more than six days.

In one embodiment, the pharmaceutical composition is adapted for administration during at least one week, such as during at least two weeks, such as during at least three weeks, such as during at least four weeks.

In one embodiment, the pharmaceutical composition is adapted for administration for at least once daily during at least a week.

In one embodiment, the pharmaceutical composition is formulated to release the compound according to Formula I over an extended period of time, such as over at least 4 hours, such as over at least 6 hours, such as over at least 24 hours after administration.

Method for Prevention and/or Reduction of Biofilm Formation

In one aspect, the present invention concerns a method for prevention and/or reduction of biofilm formation, wherein the method comprises administration of a compound of Formula I. The term "biofilm" as used herein refers to an aggregate of microorganisms in which microbial cells adhere to each other and/or to a surface. These adherent cells are often covered with a matrix of extracellular polymeric substance, e.g. comprising extracellular DNA, proteins, and polysaccharides, which is produced by the cells. Microbial cells growing in a biofilm are often physiologically distinct from planktonic cells of the same organism.

Such biofilms may form on any living or non-living surfaces. In one embodiment, the biofilm is a biofilm in or on a mammal.

In one embodiment, the biofilm is a biofilm of an implant or prosthesis. The term "implant or prosthesis" as used herein refers to artificial substitutes for body parts, and materials inserted into tissue for functional, cosmetic, or therapeutic purposes. Implants or prostheses can be functional, as in the case of artificial arms and legs, or cosmetic, as in the case of an artificial eye. Implants, all surgically inserted or grafted into the body, tend to be used therapeutically.

Said implant or prosthesis may be selected form the group consisting of catheter, peripheral venous catheter, central venous catheters, heart valves, ventricular assist devices, coronary stents, neurosurgical ventricular shunts, implantable neurological stimulators, arthro-prostheses, fracture-fixation devices, inflatable penile implants, breast implants, cochlear implants, intra-ocular lenses, dental implants, implant for laryngectomy, implant for tracheostomy, voice prosthesis, implant for jaw mobility, implant for tympanostomy, and teeth implants.

Method for Use in Preventing Preterm Birth

In one embodiment, the microbial infection is bacterial vulvovaginitis. With cervical ripening or cervical insufficiency, the said infection may migrate to the uterus and cause chorioamnionitis and subsequently preterm birth. There is evidence supporting that excessive inflammation, such as a vaginitis or cervicitis, through prostaglandin production can cause premature contractions and preterm birth even in the absence of manifest chorioamnionitis. The preterm neonate can subsequently face invasive bacterial infection; pneumonia, meningitis or sepsis, due to neonatal immunodeficiency in the preterm infant. Especially group A and B streptococci and multiresistent bacteria can give rise to serious perinatal infection in the infant and postpartum endometritis in the newly delivered woman and be the cause of both neonatal and maternal serious morbidity and mortality.

In another embodiment, the microbial infection is vulvovaginal candidosis. The preterm neonate may face invasive *Candida* infection, one of the most serious nosocomial infections causing higher morbidity and mortality than bacterial infection, in particular in neonatal intensive care units.

Thus, in one aspect, the present invention concerns a compound of Formula I for use in preventing preterm birth. In a preferred embodiment, said compound is administered vaginally. The compound may be formulated as a tampon, vagitorium, vaginal aerosol, vaginal cup, vaginal gel, vaginal insert, vaginal patch, vaginal ring, vaginal sponge, vaginal suppository, vaginal cream, vaginal emulsion, vaginal foam, vaginal lotion, vaginal ointment, vaginal powder, vaginal shampoo, vaginal solution, vaginal spray, vaginal suspension, vaginal tablet, vaginal rod, vaginal disc, vaginal device, and any combination thereof, or wherein the compound is present on a sanitary article, such as a tampon, a sanitary napkin, an incontinence pad or diaper, or a panty liner.

EXAMPLES

Example 1: Effects of Different Hydroxylated Carboxylic Acids

Biofilm Formation Assay

Yeast strains (Table 1) were grown at 37° C. in complete medium YPD (0.5% yeast extract, 1% peptone, 2% glucose) or minimal medium consisting of YNB (yeast nitrogen base without amino acids and ammonium sulphate, FORMEDIUM™, CYN0505) supplemented with 0.5% ammonium sulphate, 0.2% glucose and 100 mM L-proline. If needed 2% agar was used to solidify media. The liquid minimal medium (YNB (yeast nitrogen base without amino acids and ammonium sulphate, FORMEDIUM™, CYN0505) supplemented with 0.5% ammonium sulphate, 0.2% glucose and 100 mM L-proline) was used for biofilm assay (biofilm medium).

In the experiments on the impact of pH on biofilm the pH values (from 2.6 to 6.6) were obtained using either different potassium phosphate buffers at the final concentration 0.25 M, or by the addition of citric acid, lactic acid, and gluconic acid to the biofilm medium.

TABLE 1

Yeast strains used in this study.

| Original name | Laboratory strain designation | Description | Reference |
|---|---|---|---|
| Candida albicans SC5314 | Y775 | Wild-type, virulent in a mouse model of systemic infection, sequenced strain | [A. M. Gillum, et al. Mol. Gen. Genet. 1984, 198, 179-182] |
| Candida glabrata CBS138 | Y1092 | Wild-type, type strain isolated from human feces, sequenced strain | [B. Dujon, et al. Nature, 2004, 430, 35-44] |

Biofilm was measured in liquid culture as described [K. Scherz et al., G3 (Bethesda), 2014, 4, 1671-1680. I. Serrano-Fujarte et al. Biomed Res Int. 2015; 2015:783639] with some modifications. Prior the biofilm assay, yeast cultures were grown in liquid YPD medium for 24 hours until stationary phase ($OD_{600}$ 11-17)[2], cells were then pelleted by centrifugation (1699 g), washed with sterile water and cells were further inoculated into test biofilm medium (YNB (yeast nitrogen base without amino acids and ammonium sulphate) supplemented with 0.5% ammonium sulphate, 0.2% glucose and 100 mM L-proline pH7.0) at final concentration 0.2 $OD_{600}$/ml and incubated in 96-well flat-bottom polystyrene microtiter plates (Sigma Aldrich, Corning® Costar® culture plates, CLS3596-50EA) for 72 hours at 37° C. thermostat. At defined time points crystal violet (HT901-8FOZ; Sigma Aldrich) was added to the media at the final concentration 0.05%, in addition total biomass was measured. After 24 hours of cells staining, plate wells were washed four times with 200 μl of water to remove planktonic cells, biofilms were then dried and dissolved in 200 μl of 96% ethanol. Total biomass and crystal violet biofilm staining measurements were performed at $OD_{560}$ with FLUOstar OPTIMA plate reader, BMG LABTECH. Crystal violet biofilm measurements were normalized to the total biomass ($OD_{560}$Biofilm/$OD_{560}$ total biomass).

Effects of Different Hydroxylated Carboxylic Acids

To compare the effects of different hydroxylated carboxylic acids at low concentrations, the biofilm formation was measured 24 h after addition of 0.06 wt % of glyceric acid, xylonic acid, citric acid, gluconic acid, and lactic acid, under unbuffered conditions. The data are shown in Table 2 and in FIG. 1.

TABLE 2

Effect of low concentrations (0.06%) of hydroxylated carboxylic acids on the biofilm formation of *Candida albicans*. The biofilm was measured after 24 h.

| | resulting pH | normalized biofilm (% of control) |
|---|---|---|
| glyceric acid (GlyA) | 7.0 | 40 |
| xylonic acid (XA) | 7.0 | 31 |
| citric acid (CA) | 4.6 | 14 |
| gluconic acid (GA) | 6.5 | 6 |
| lactic acid (LA) | 4.9 | 13 |

As can be seen from Table 2, gluconic acid is the most efficient compound, followed by lactic acid and citric acid.

Replacing lactic acid by gluconic acid resulted in >50% less biofilm formation (6% vs 13% of control). Given that the biofilm formation is very sensitive to low pH and that gluconic acid only induces a moderate lowering of the pH in comparison with lactic acid and citric acid, the result is striking.

Example 2: Biofilm Formation of *Candida albicans* at Different pH

In order to further evaluate the effect of gluconic acid in preventing biofilm formation, the biofilm formation at different pH were determined (as described in Example 1) for gluconic acid, lactic acid and citric acid.

As can be seen from Table 3, Gluconic acid shows strong effects on the biofilm formation of *Candida albicans*, while the effects from lactic acid and citric acid are much less pronounced. Furthermore, gluconic acid shows strong effect also at pH values up to around at least 6, whereas the effect seen with lactic acid and citric acid starts diminishing already at pH 5. In addition, gluconic acid results in a complete loss of biofilm formation at pH 2.6. The data are summarized in Table 3.

TABLE 3

Biofilm formation of *Candida albicans* by addition of gluconic acid, lactic acid or citric acid (24 h treatment).

|  | gluconic acid | lactic acid | citric acid | buffer |
|---|---|---|---|---|
| normalized biofilm ($OD_{560}$) at pH 6.1 | 0.17 | 3.1 | 4.6 | 3.2 |
| normalized biofilm ($OD_{560}$) at pH 2.6 | 0 | 1.6 | 0.34 | 0.25 |

Example 3: Biofilm Formation of *Candida glabrata* at Different pH

*Candida glabrata* is much more complicated to treat, compared to *Candida albicans*. However, a clear effect is obtained by longer treatment, i.e. 72 h with gluconic acid (Table 4).

TABLE 4

Biofilm formation of *Candida glabrata* by addition of gluconic acid, lactic acid or citric acid.(72 h treatment).

|  | gluconic acid | lactic acid | citric acid | buffer |
|---|---|---|---|---|
| normalized biofilm ($OD_{560}$) at pH 6.1 | 1.6 | 2.8 | 2.9 | 4.7 |
| normalized biofilm ($OD_{560}$) at pH 2.6 | 0.07 | 0.9 | 1.0 | 4.8 |

Based on these results it was concluded that gluconic acid has superior effect in targeting biofilm formation by *candida* compared to lactic acid and citric acid. In contrast to the effect observed for lactic acid and citric acid, the effect observed for gluconic acid is not merely a pH-related effect. The effect is present even at pH 6.

It is thus concluded that gluconic acid is useful as antifungal compound, as indicated by reduction of biofilm formation. The compound is physiologically and pharmaceutically acceptable. Gluconic acid is thus useful for providing pharmaceutical formulations for use in treating vulvovaginal candidosis.

Example 4: Preparation of Gluconic Acid Derivatives

Lactonization/Oligomerization of Gluconic Acid:

Gluconic acid (GA) (50 wt % in $H_2O$, 4 g) was poured in an open vial and heated to 120° C. After 24 h, the mixture was cooled down to room temperature, whereas it solidified.

In order to analyze the composition of aqueous solution of gluconic acid (GA), GA (50 wt % in $H_2O$) was dissolved in DMSO-$d^6$ and analyzed by $^1$H- and $^{13}$C-NMR. Lactonized/oligomerized gluconic acid (cf. above) was dissolved in DMSO-$d^6$ and analyzed by $^1$H- and $^{13}$C-NMR, see Table 5.

TABLE 5

Composition of GA, lactonized and oligomerized GA, analyzed by $^1$H- and $^{13}$C-NMR.

| Compound | DMSO-$d^6$ ($^1$H and $^{13}$C) |
|---|---|
| GA [526-95-4] | 70% gluconic acid |
|  | 15% glucono-δ-lactone |
|  | 15% γ-gluconolactone |
| Lactonized and oligomerized GA | 10% gluconic acid |
|  | 25% δ-gluconolactone |
|  | 50% γ-gluconolactone |
|  | 15% oligomerized material |

It was concluded that the GA form a complex mixture of different lactones as well as oligomerized material upon prolonged dehydration.

Example 5: Hydrolysis of Glucono-δ-Lactone (GDA)

In water solution glucono-δ-lactone (GDA) is in equilibrium with gluconic acid (GA, CAS 526-95-4). GDA (200 mg) was added to distilled $H_2O$ (20 mL), pH 4 buffer, pH 5 buffer, or pH 7 buffer at 37° C. The optical rotation and pH were measured over time. Optical rotation, measured at 37° C., sodium D line, C=10 mg/mL, path length=10 cm. The optical rotation of GDA is approximately 66°. The optical rotation of gluconic acid is approximately 5° [D. T. Sawyer, J. B. Bagger, J. Am. Chem. Soc., 1959, 81, 5302-5306].

Figure 2:
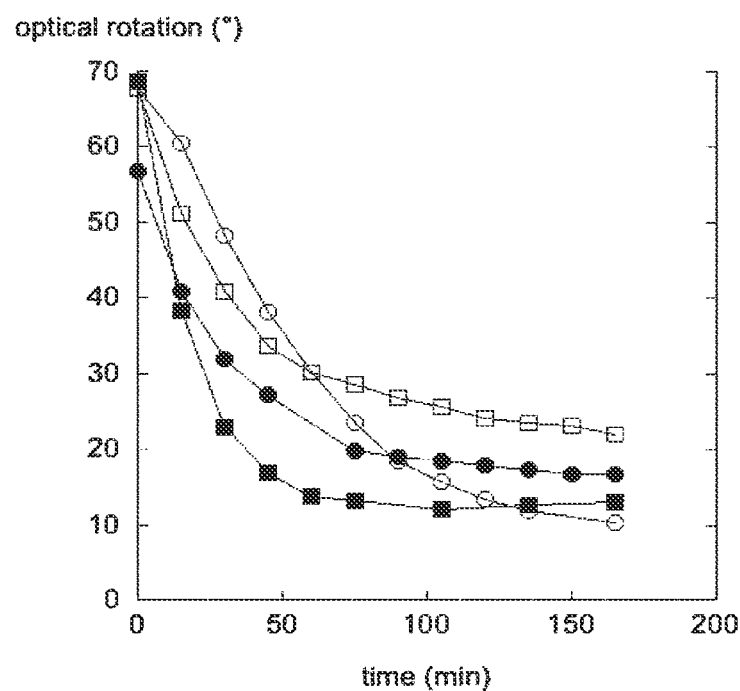
FIG. 2. Changes in optical rotation in the hydrolysis of glucono-δ-lactone (GDA) in distilled water (unfilled circles), pH 4 buffer (filled squares), pH 5 buffer (unfilled squares), and pH 7 buffer (filled circles).
Figure 3:
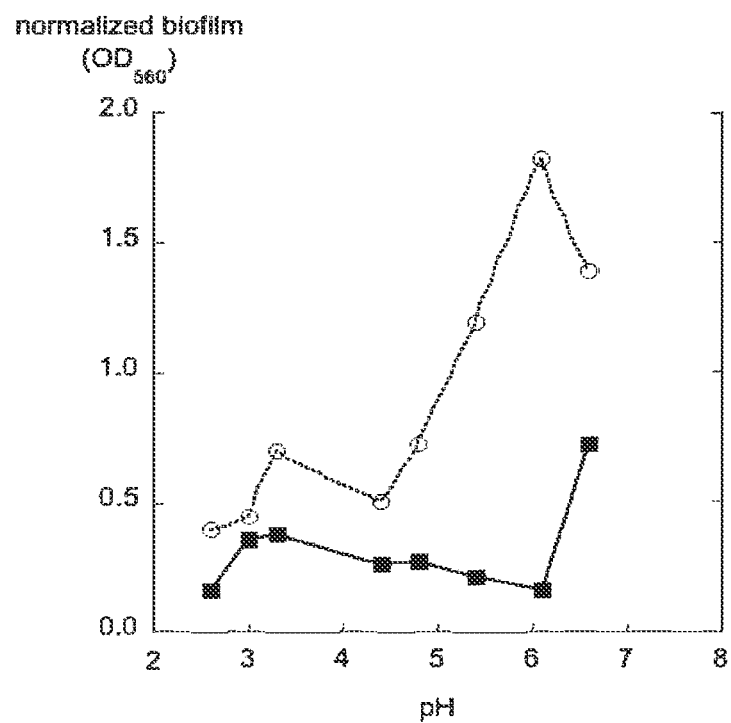
FIG. 3. Normalized biofilm formation of Candida albicans in the minimal media at pH 2.6-6.6 with phosphate buffer (unfilled circles, dotted line) or glucono-δ-lactone (filled squares, solid line). The biofilm was measured after 24 h and the staining was performed with crystal violet.

This experiment shows that GDA is slowly hydrolyzed to a mixture of GDA and GA (FIG. 2). The equilibrium is pH-dependent and relevant concentrations of GDA are present at all buffered conditions.

Example 6: Biofilm Formation in a Model of In Vivo Conditions Using Gluconic Acid (GA)

Figure 4:
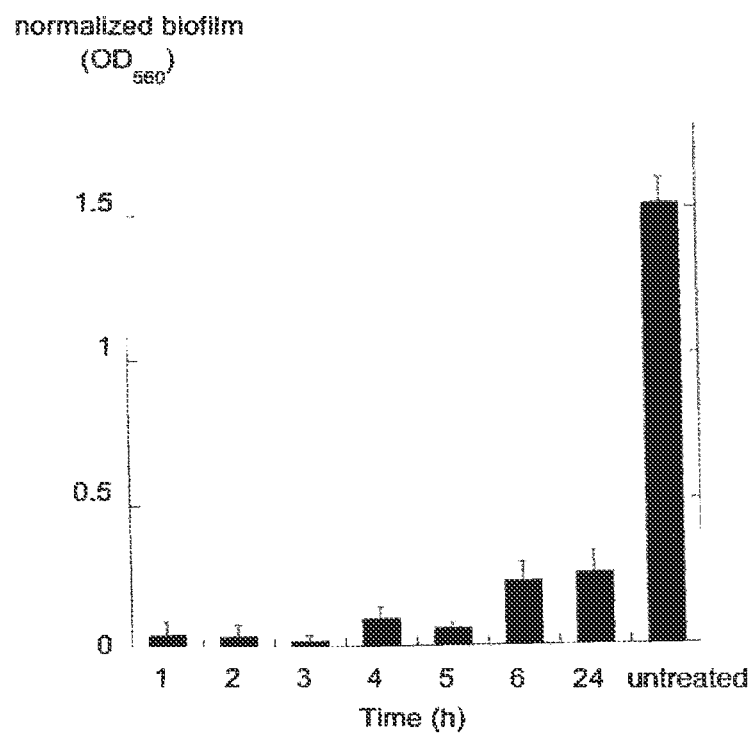
FIG. 4. (A) Normalized biofilm formation of Candida albicans treated with lactonized/oligomerized GA. A pellet of lactonized/oligomerized gluconic acid was added to a buffer solution of pH 3.71 (10 mL) at 37° C. Samples (4 mL) were taken every hour (at different time interval) and new buffer solution (4 mL) was added. The samples were diluted 50 times with biofilm medium and the amount of biofilm formation was measured after 24 h. (B) Normalized biofilm formation of Candida glabrata treated with lactonized/oligomerized GA. A pellet of lactonized/oligomerized gluconic acid was added to a buffer solution of pH 3.71 (10 mL) at 37° C. Samples (4 mL) were taken every hour (at different time interval) and new buffer solution (4 mL) was added. The samples were diluted 50 times with biofilm medium and the amount of biofilm formation was measured after 24 h.
Figure 4:
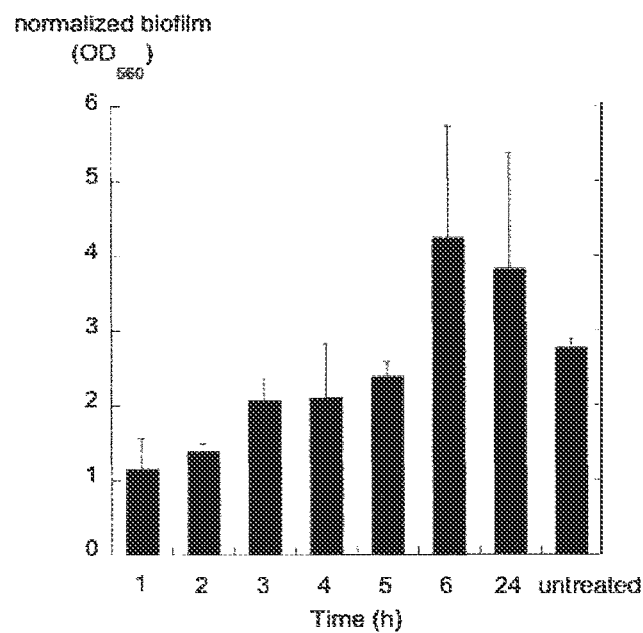

Pellet of lactonized/oligomerized gluconic acid (1.3 g, duplicate samples) were added to buffer solution of pH 3.71 (0.5 M $KH_2PO$/ortho phosphoric acid, 10 mL) at 37° C. Samples (4 mL) were taken every hour (1, 2, 3, 4, 5, 6 and 24 h) and new buffer solution (4 mL) was added. The samples were diluted 50 times with biofilm medium (vide supra) and the amount of biofilm formation was measured after 24 h as described above. As seen from FIG. 4A, the released GA significantly reduces the amount of biofilm formation in *Candida albicans*. Further, the hydrolysis of the pellet is seemingly slow enough to provide a preventive effect for at least up to 6 hours, likely far more. The effect is less pronounced with *Candida glabrata* (FIG. 4B). The data are summarized in Table 6.

TABLE 6

Biofilm formation of Candida albicans and Candida glabrata treated with lactonized/oligomerized GA in a model of in vivo conditions. Samples were taken after 1 h, diluted 50 times with biofilm medium and the amount of biofilm formation was measured after 24 h.

| | normalized biofilm (% of control), 1 h |
|---|---|
| Candida albicans | 6.5 |
| Candida glabrata | 42 |

Figure 5:
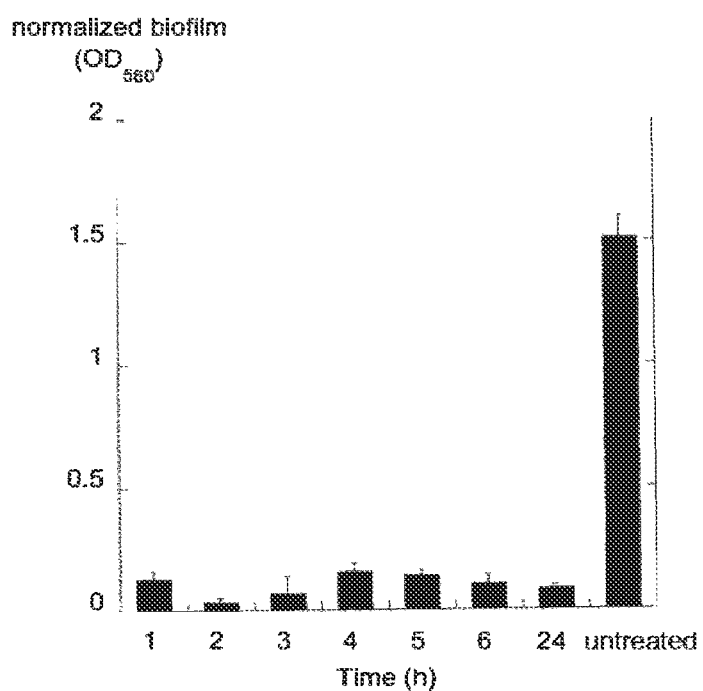
FIG. 5. (A) Normalized biofilm formation of Candida albicans treated with glucono-δ-lactone (GDA). A pellet of GDA was added to a buffer solution of pH 3.71 (10 mL) at 37° C. Samples (4 mL) were taken after 1, 2, 3, 4, 5, 6 and 24 hours and new buffer solution (4 mL) was added. The samples were diluted 50 times with biofilm medium and the amount of biofilm formation was measured after 24 h. (B) normalized biofilm formation of Candida glabrata treated with GDA. A pellet of GDA was added to a buffer solution of pH 3.71 (10 mL) at 37° C. Samples (4 mL) were taken after 1, 2, 3, 4, 5, 6 and 24 hours and new buffer solution (4 mL) was added. The samples were diluted 50 times with biofilm medium and the amount of biofilm formation was measured after 24 h.
Figure 5:
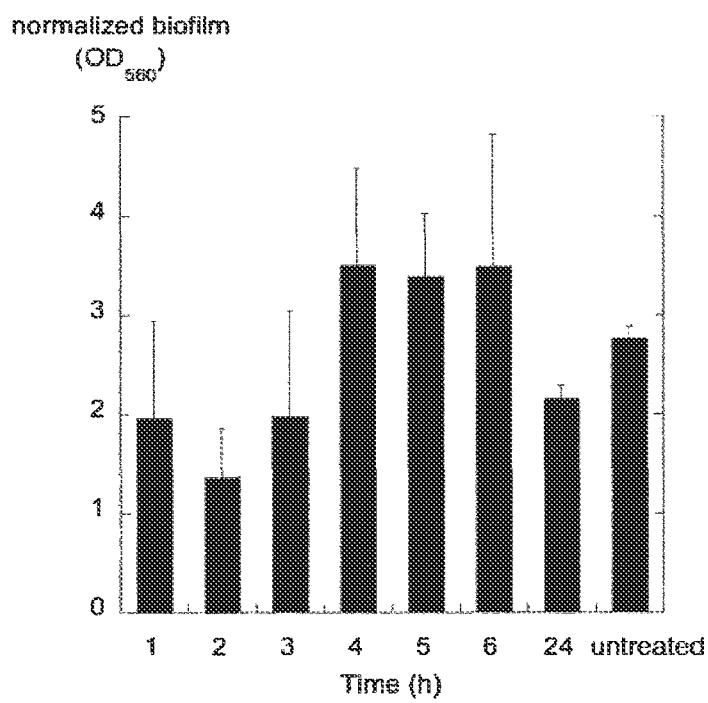

Example 7: Biofilm Formation in a Model of In Vivo Conditions Using Glucono-δ-Lactone Pellets of glucono-δ-lactone (GDA) (2.5 g, duplicate samples) were added to buffer solution of pH 3.71 (0.5 M $KH_2PO_4$/ortho phosphoric acid, 10 mL) at 37° C. Samples (4 mL) were taken at fixed time points (1, 2, 3, 4, 5, 6 and 24 h) and new buffer solution (4 mL) was added. The samples were diluted 50 times with biofilm medium (vide supra) and the amount of biofilm formation was measured after 24 h as described above. As seen from FIG. 5A, the released GDA significantly reduces the amount of biofilm formation in C. albicans. Further, the hydrolysis of the pellet is seemingly slow enough to provide a preventive effect for at least up to 24 hours, likely far more. The effect is less pronounced with C. glabrata (FIG. 5B).

TABLE 7

Biofilm formation of C. albicans and C. glabrata treated with GDA in a model of in vivo conditions. Samples were taken after 1 h, diluted 50 times with biofilm assay medium and the amount of biofilm formation was measured after 24 h.

| | Normalized biofilm (% of control), 1 h |
|---|---|
| Candida albicans | 8.3 |
| Candida glabrata | 71 |

The results show that biofilm formation of both C. albicans and C. glabrata was reduced in the presence of GDA. In addition to diminished biofilm formation, GDA may affect the viability of mature biofilm of C. albicans and C. glabrata.

Example 8: Viability of Mature Biofilms of C. albicans and C. glabrata Treated with Glucono-δ-Lactone Viability of biofilms of C. albicans and C. glabrata after treatment with glucono-δ-lactone (GDA) at different concentration and different time periods was evaluated by staining the cells with XTT. XXT is a colorimetric assay for quantification of cellular viability, and cytotoxicity. The assay is based on the cleavage of the tetrazolium salt XTT, a conversion that only occurs in viable cells. The mature biofilm was exposed to GDA for 24 h. Then the cells were washed 2 times with PBS, after which the XTT reaction mixture was added. After 30 min the optical density measured at 485 nm.

Figure 6:
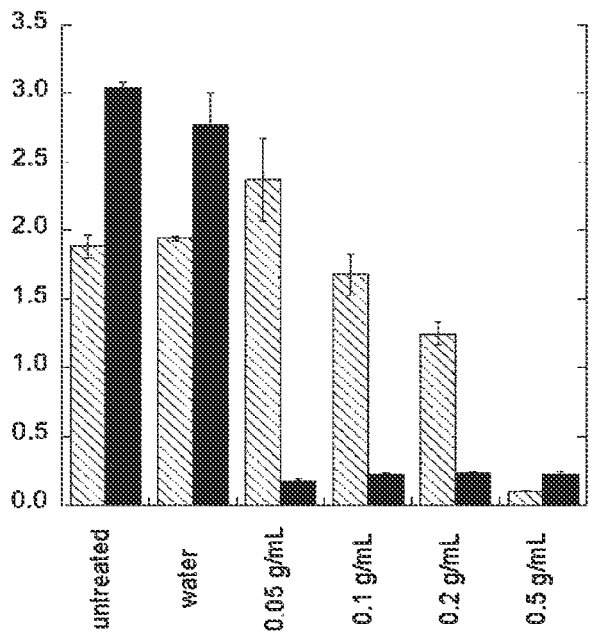
FIG. 6. (A) Viability of biofilms of C. albicans and C. glabrata after treatment with glucono-δ-lactone (GDA) at different concentrations for 24 h. The biofilm staining was performed with XTT. Optical density measured at 485 nm. Diagonal stripes indicate data for C. albicans. Filled black columns indicate data for C. glabrata. (B) Viability of biofilms of C. albicans and C. glabrata after treatment with GDA at different concentrations for 48 h. The biofilm staining was performed with XTT. Optical density measured at 485 nm. Diagonal stripes indicate data for C. albicans. Filled black columns indicate data for C. glabrata.
Figure 6:
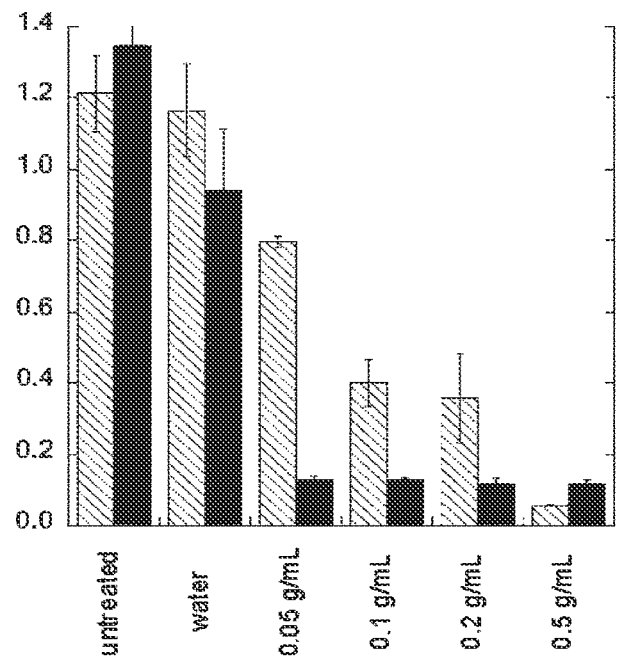

The XTT assay showed a strong decrease in viability for C. glabrata already after 24 h of incubation (FIG. 6A). The effect was less pronounced for C. albicans but clearly seen after 48 h (FIG. 6B).

Figure 7:
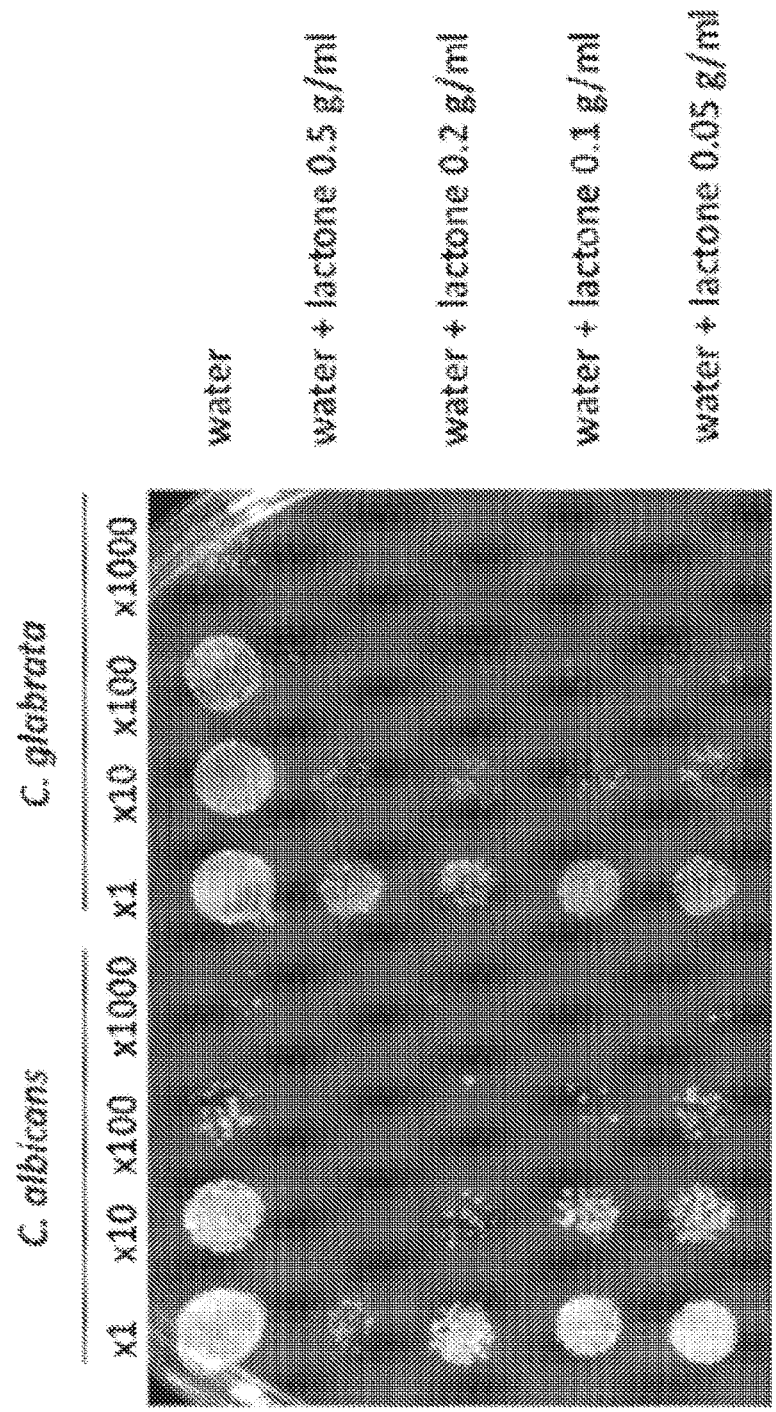
FIG. 7. Effect of glucono-δ-lactone (GDA) on mature biofilm of C. albicans and C. glabrata. Mature biofilm (grown for 48 h) was incubated with GDA for 5 h at 37° C. and then cells at serial dilution were plated on YPD plate to estimate cell survival.

Furthermore, mature biofilm (grown for 48 h in YNB, 0.2% glucose, 100 mM proline) of C. albicans and C. glabrata was incubated with GDA of different concentrations (0.05-0.5 g/ml) at 37° C. For this purpose biofilm medium (YNB, 0.2% glucose, 100 mM proline) was removed and GDA was added, which was dissolved either in water at concentration 0.05, 0.1, 0.2 and 0.5 g/ml. After incubation with GDA for 5 h or 73 h, 5 μl of cells were plated at serial dilution (1:10 to 1:1000) on the agar medium YPD to estimate cell survival. The plated cells were incubated for 24 h at 37° C. and visually analyzed. The cells from the mature biofilm treated with water were used as a control. It was found that the GDA decreases cell viability of C. albicans and C. glabrata, particularly at high concentrations. At the concentrations of 0.2 and 0.5 g/ml after 5 h of incubation the cell viability was decreased by about 100 times for both C. albicans and C. glabrata. After 73 h of incubation with 0.5 g/ml of GDA the cell viability of C. albicans was decreased by about 1000 times (data not shown). C. glabrata proved to be more sensitive to GDA (FIG. 7).

Example 9: Microfluidics Study of Biofilm Development

Figure 8:
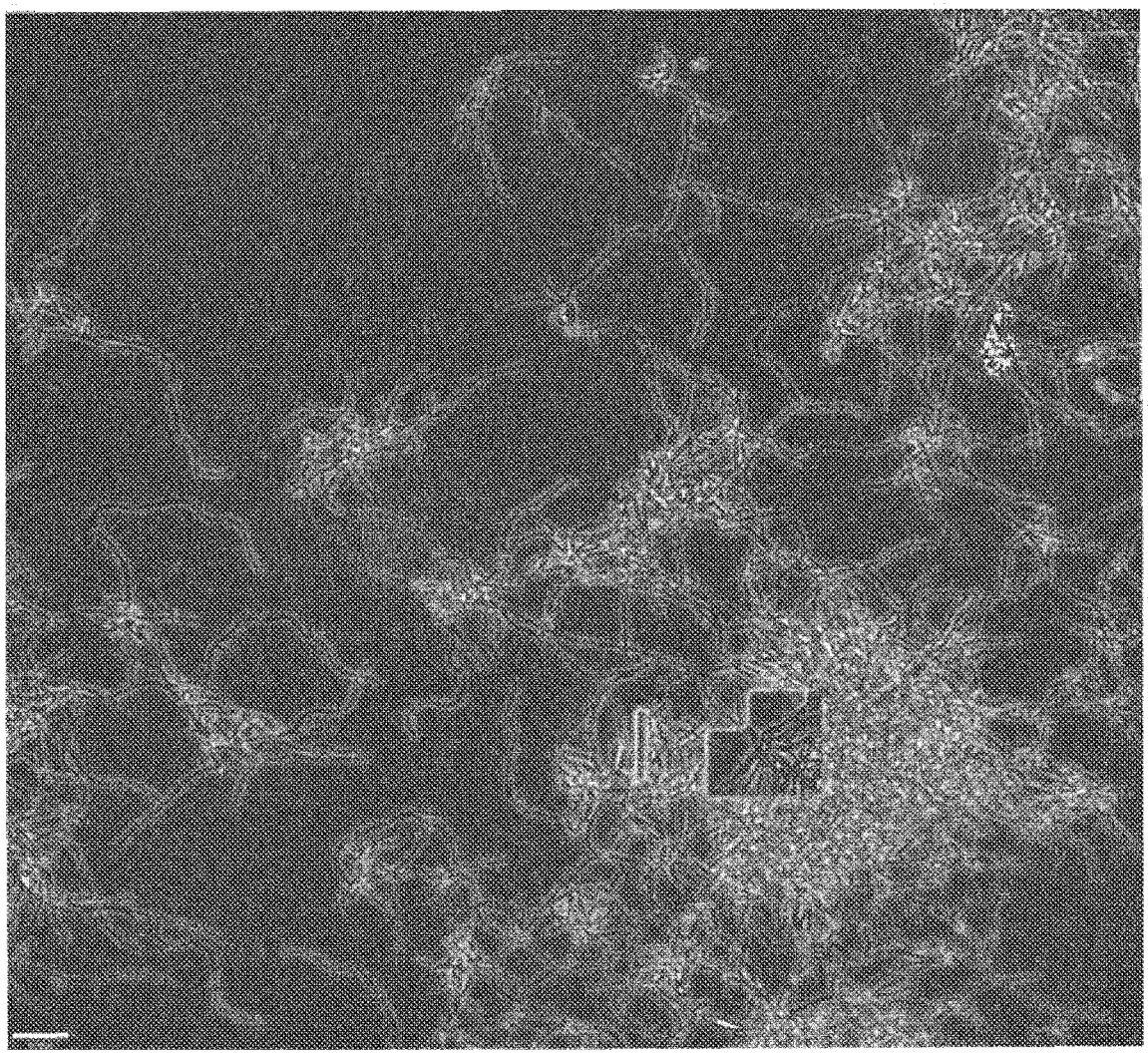
FIG. 8. (A) Microfluidics study of biofilm development of untreated C. albicans in minimal medium pH 7.0. The untreated cells mainly form hyphae. (B) Microfluidics study of biofilm development of C. albicans treated in minimal medium with a hydrolysate of glucono-δ-lactone (GDA) at ×50 final concentration pH 3.8. The addition of GDA caused C. albicans to grow predominantly as yeast form, but not as hyphae.
Figure 8:
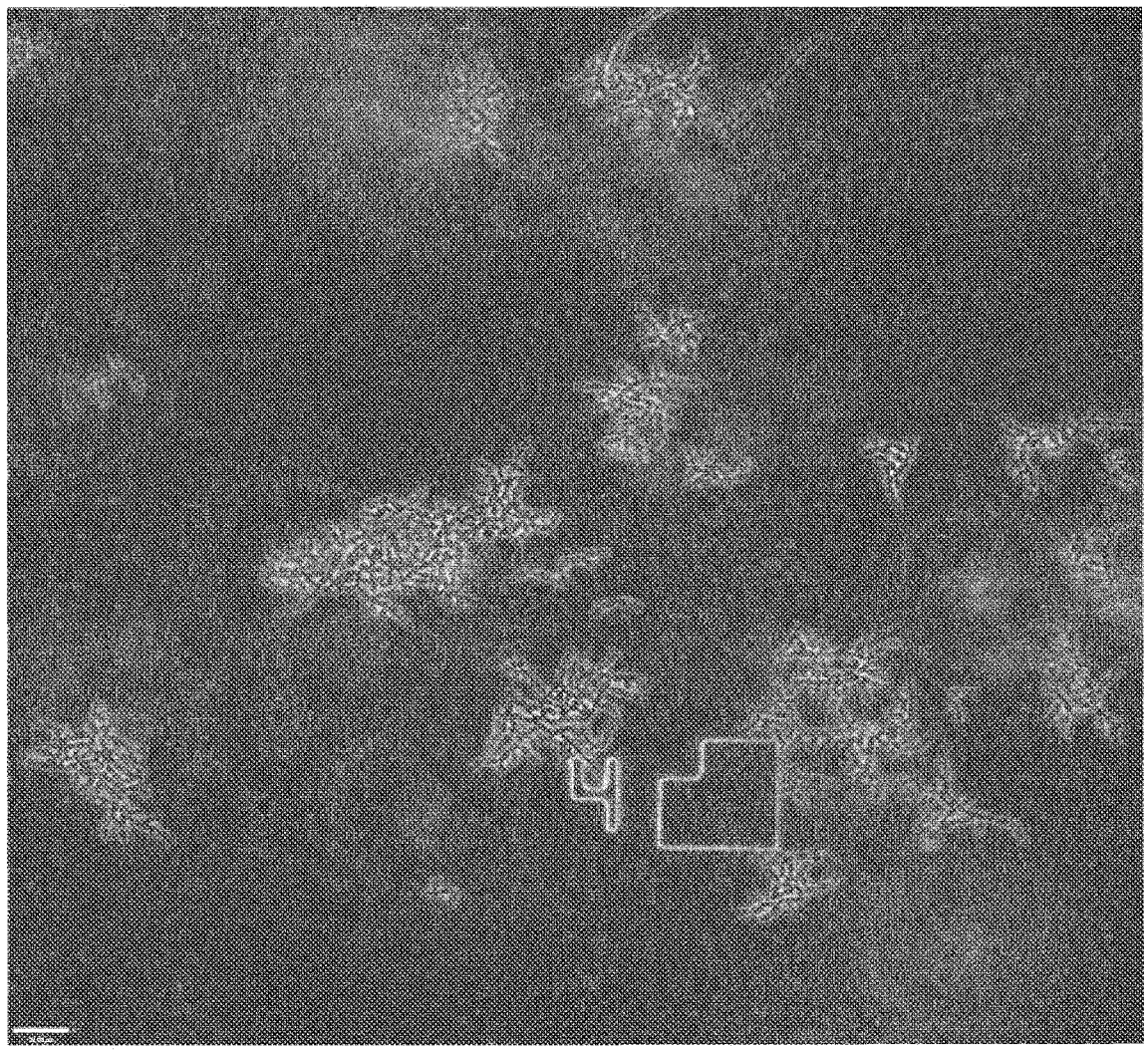

To monitor the C. albicans cell morphology we studied the biofilm development also using microscopy and microfluidics. After the yeast cells were inoculated, hyphae started to form within first hour of incubation in the biofilm medium (YNB supplemented with 100 mM proline and 0.2% glucose, pH7.0). FIG. 8A shows untreated cells after 5 h. A pellet of glucono-δ-lactone (2.5 g) was added to buffer solution of pH 3.71 (0.5 M $KH_2PO_4$/ortho phosphoric acid, 10 mL) at 37° C. A sample was taken after 1 h and diluted 50 times with biofilm medium and added to C. albicans. After 5 h most treated cells were planctonic (FIG. 8B).

Example 10: Viability of Different Candida Species in the Presence of Glucono-δ-Lactone Other Candida sp. studied were also sensitive (i.e. cell viability measure using the XTT assay, cf Example 8) to glucono-δ-lactone (GDA). However, they displayed different levels of sensitivity. Candida albicans SC5314 displayed the lowest susceptibility and Candida krusei silicone isolate A4-1 displayed the highest susceptibility. The GDA-toxicity is mediated through cell wall damage as the cells exposed to GDA had lower viability on the medium with calcofluor white compared to that supplemented with osmotic stabilizer (0.5M sucrose) and compared to the untreated cells on these media. Table 3 summarizes qualitative effects shown by GDA.

TABLE 8

Sensitivity of different Candida species to GDA

| Strain | Sensitivity to GDA, 24 h exposure, plates |
|---|---|
| C. albicans SC5314 | + |
| C. glabrata CBS138 | ++++++ |
| C. tropicalis silicone isolate U3-3 | ++++++++ |
| C. krusei silicone isolate U3-5 | ++ |
| C. tropicalis silicone isolate A6-1 | +++ |
| C. krusei silicone isolate U2-12 | ++++++++ |
| C. krusei silicone isolate A5-2 | ++ |
| C. krusei silicone isolate A4-1 | +++++++++ |

To conclude, (i) GDA can break mature biofilm formed by *C. albicans* and *C. glabrata*, (ii) upon exposure to GDA, *C. albicans* transforms into yeast form, while the viability of *C. glabrata* decreases, (iii) the effect is clear even on other strains, i.e. *C. tropicalis* and *C. krusei*.

Example 11: Cooligomerisation of Gluconic Acid (GA) with Lactic Acid (LA)

LA: GA (4:1 Mole Ratio)

DL-Lactic acid (563 mg, 6.26 mmol) and D-gluconic acid (50% in water, 0.50 mL, 1.57 mmol) was mixed in a test tube and heated to 130° C. After 4 h, the temperature was increased to 140° C. After a total of 27 h, the reaction mixture was allowed to reach rt. The reaction mixture solidified upon cooling.

LA: GA (8:1 Mole Ratio)

DL-Lactic acid (569 mg, 6.32 mmol) and D-gluconic acid (50% in water, 0.25 mL, 0.78 mmol) was mixed in a test tube and heated to 130° C. After 4 h, the temperature was increased to 140° C. After a total of 27 h, the reaction mixture was allowed to reach rt. The reaction mixture solidified upon cooling.

LA: GA (16:1 Mole Ratio)

DL-Lactic acid (565 mg, 6.28 mmol) and D-gluconic acid (50% in water, 0.35 mL, 0.39 mmol) was mixed in a test tube and heated to 130° C. After 4 h, the temperature was increased to 140° C. After a total of 27 h, the reaction mixture was allowed to reach rt. The reaction mixture solidified upon cooling.

LA: GA (10:1 Mole Ratio, Direct Mixing)

DL-Lactic acid (1 g, 11 mmol) and D-gluconic acid (50% in water, 0.35 mL, 0.78 mmol) were mixed in a test tube and heated to 130° C. under vacuum. After a total of 22 h, the reaction mixture was allowed to reach rt. The reaction mixture became almost totally solid upon cooling.

LA: GA (10:1 Mole Ratio, Pre-Heating for 5 h)

DL-Lactic acid (1 g, 11 mmol) was pre-heated at 130° C. under vacuum. After for 5 h, D-gluconic acid (50% in water, 0.35 mL, 1.1 mmol) was added. After another 16 h under vacuum at 130° C., the reaction mixture was allowed to reach rt. The reaction mixture solidified upon cooling.

1 Wt % CA in GA

D-gluconic acid (50% in water, 4 g) and citric acid monohydrate (20 mg, 1 wt. %) were mixed in a test tube and heated to 120° C. After a total of 15 h, the reaction mixture was allowed to reach rt. The reaction mixture did not solidify upon cooling.

5 wt % CA in GA

D-gluconic acid (50% in water, 4 g) and citric acid monohydrate (105 mg, 5 wt. %) were mixed in a test tube and heated to 120° C. After a total of 15 h, the reaction mixture was allowed to reach rt. The reaction mixture did not solidify upon cooling.

10 wt % CA in GA

D-gluconic acid (50% in water, 4 g) and citric acid monohydrate (222 mg, 10 wt. %) were mixed in a test tube and heated to 120° C. After a total of 15 h, the reaction mixture was allowed to reach rt. The reaction mixture did not solidify upon cooling.

From these results we show that gluconic acid can be oligomerized with lactic acid to form a solid, in contrary to pure gluconic acid or lactic acid that both are liquids.

Example 12: Effect of Glucono-δ-Lactone and Sugar Acids on *E. coli*

Growth Conditions

The bacterial strain *Escherichia coli* K12 was used for the biofilm study. This strain was maintained on LB medium at 37° C. The biofilm was studied in synthetic medium M9 (×1 M9 minimal salts (Sigma M6030), 2 mM $MgSO_4$, 0.1 mM $CaCl_2$, and 0.2% glucose), which contained either phosphate buffer, citric acid, lactic acid, gluconic acid or glucono-O-lactone to obtain media with different pH (2.6-6.6).

Biofilm

The overnight culture of *E. coli* K12 ($OD_{600}$~5.0) was washed with sterile water and inoculated to the final concentration 0.2 OD/ml of M9 medium with different pH of different compounds. The biofilm development was studied in 96-well flat-bottom polystyrene microtiter plates (Sigma Aldrich, Corning® Costar® culture plates, CLS3596-50EA). The biofilm was stained with crystal violet.

Figure 9:
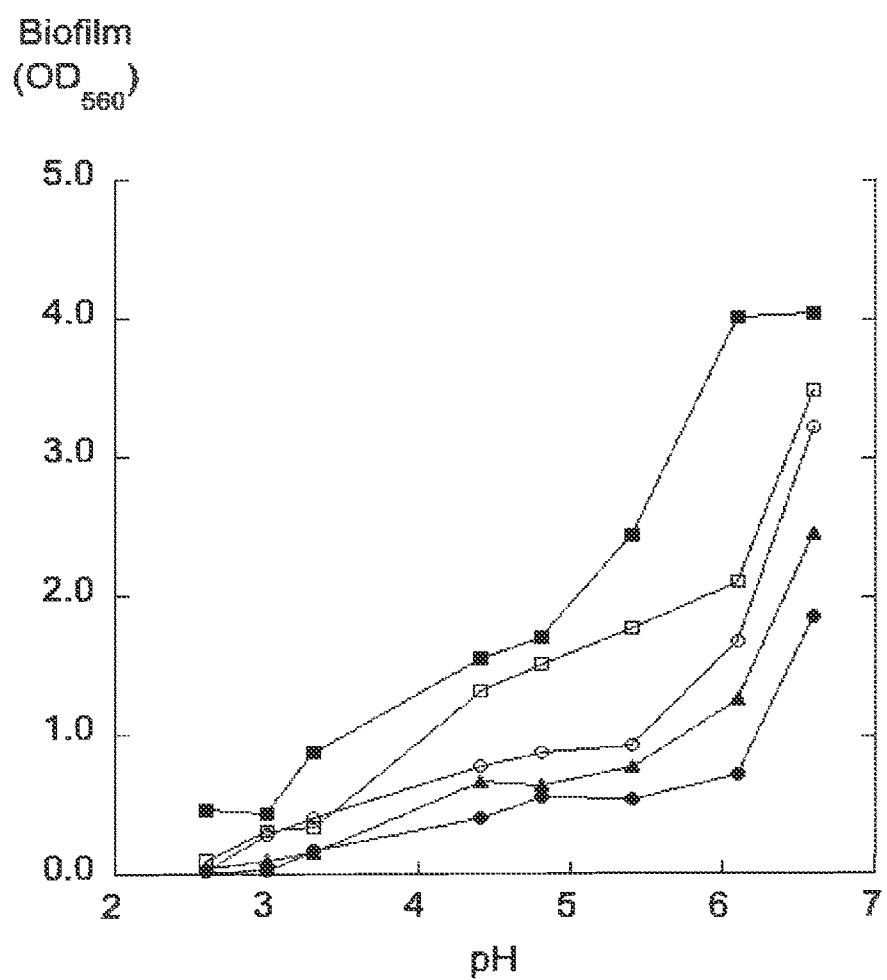
FIG. 9. Biofilm formation of Escherichia coli K12 treated with either phosphate buffer (filled squares), citric acid (unfilled squares), lactic acid (filled triangles), gluconic acid (filled circles) or glucono-δ-lactone (unfilled circles) to obtain media with different pH (2.6-6.6). The biofilm was stained with crystal violet.

During the biofilm experiment (24-48 hours) the bacterial strain had increased its biomass (2-3-fold) only in the M9 medium supplemented with phosphate buffer at pH 6.1 and pH 6.6 (FIG. 9). The biomass was lower on other media and we observed the decrease in bacterial biomass with lowering of the pH of the medium. Acids (citric acid, lactic acid, gluconic acid), and glucono-δ-lactone had inhibiting effect on the growth. In addition to the growth inhibition, the lowering of the pH of the medium resulted in decreased biofilm formation. The lowest amount of biofilm was observed in the medium supplemented with gluconic acid. The second most effective in biofilm inhibition was lactic acid followed by glucono-δ-lactone. Comparing to the phosphate medium, the biofilm on gluconic acid medium was 38-fold lower at pH 2.6 and 15-fold lower at pH 3.0. At pH 6.6 the gluconic and lactic lowered the biofilm ~2-fold. The glucono-δ-lactone at pH 2.6 decreased the biofilm formation 14.2 times at 24 h and 30 times at 48 h correspondingly.

The lowering of pH of the media had clear effect on the *E. coli* biofilm development, which is likely associated with bactericidal effect (the lower biofilm was accompanied with lower biomass).

Example 13: MIC Test of Glucono-δ-Lactone on *Gardnerella vaginalis, Lactobacillus Crsipatus*, and *Lactobacillus iners*

Strains

*Gardnerella vaginalis* CCUG 3717
*Lactobacillus* crispatus CCUG 44128
*Lactobacillus iners* CCUG 44025

Preparation of Inoculums

*Gardnerella vaginalis, Lactobacillus iners*, and *Lactobacillus* crispatus were recovered by CCUG (Culture Collection of University of Gothenburg). Subculture plates were made for *G. vaginalis* on Chocolate-GL plates and *Lactobacillus* spp. on M.R.S. agar plates at 5% $CO_2$, 36° C. The inoculums were prepared from the subculture plates. Colonies were inoculated to culture tubes with 5 ml test medium and vortexed 2 min with about 10 glass beads a 3 mm in diameter. Colonies were taken until the turbidity of the solution was $OD_{475}$ of 0.4-0.5. The bacterial solutions were checked in light microscopy at ×40 with phase contrast to make sure that the cells were dispersed. Each bacterial suspension was diluted in its test medium, 1:100, to equal 1-3×$10^6$ CFU/ml. The microbial solutions were stored at 20° C. during the preparation of the inoculums Microdilution Preparation and the MIC Test The test substance solution was prepared aseptically at 1 g/ml in sterile $H_2O$. The first row of wells was filled with 100 µl substance and then 2 fold dilutions were done vertically in 8 steps. Controls were included: i) Growth controls for each strain (+ctrl)=respective microorganism in test medium without antimicrobial agent (AM), ii) no growth control (−ctrl)=test medium and substance at highest concentration tested, this is to make sure that the substance alone does not generate a colour change of test media, iii) gentamicin control for each strain Next, 100 µl microorganisms were added and the plates were gently shaken at 500 rpm for 30 seconds before incubation at 35° C. and 90% RH in the $CO_2$ incubator set at 5% $CO_2$. After 48 and 72 hours of incubation, the OD was measured and ocular assessments were done. The pH was also measured for all dilutions, n=1, pH=6.8-7.1

MIC microdilution assays were run in triplicate to assess the MIC values for GDA against G. vaginalis (CAMHB) and L. crispatus (IsoS-M.R.S.) after 48 hours incubation at 5% $CO_2$ and L. iners cultured under anaerobic conditions after 120 hours (Table 7).

TABLE 9

Minimum inhibitory concentrations (MICs) for GDA against G. vaginalis (CAMHB), L. crispatus (IsoS-M.R.S.), and L. iners (CAMHB).

| Strain | CCUG identification | MIC (g/ml) |
|---|---|---|
| G. vaginalis | CCUG 3717 | 0.001 |
| L. crispatus | CCUG 44128 | 0.0078 |
| L. iners | CCUG 44025 | 0.0078 |

The minimum inhibitory concentration (MIC) value of GDA against *Gardnerella vaginalis* is much lower than the MIC value of GDA against *Lactobacillus iners* and *Lactobacillus crispatus*. Thus, GDA is more efficient against the *Gardnerella vaginalis* than against the benign *Lactobacillus iners* and *Lactobacillus* crispatus.

Example 14: MIC Test of GDA on *Escherichia coli, Staphylococcus Epidermidis, Staphylococcus aureus, Pseudomonas aeruginosa, Acetinobacter baumanii, Streptococcus pyogenes, Streptococcus agalactiae*, Beta-Hemolytic Streptococci Groups C and G and *Porphyromonas gingivalis*

Strains
Aerobes:
*Escherichia coli* CCUG 3274/ATCC 10536
*Staphylococcus epidermidis* CCUG 23118
*Staphylococcus aureus* CCUG 15915/ATCC 29213
*Pseudomonas aeruginosa* (PAO1) CCUG 56489/ATCC 15692
*Acetinobacter baumanii* CCUG 57035
Fastidious aerobes:
*Streptococcus pyogenes* CCUG 47803/ATCC 700294
*Streptococcus agalactiae* CCUG 29376
Beta-Hemolytic Streptococci Groups C *Streptococcus dysgalactiae* ss *equisimilis*
CCUG 4211
Beta-Hemolytic Streptococci Groups G *Streptococcus dysgalactiae* ss *equisimilis*
CCUG 7975
Anaerobe:
*Porphyromonas gingivalis* CCUG 25893/ATCC 33277

Preparation of Inoculums

All strains were recovered from microbanks and streak and subculture plates were made. The aerobes on TSA plates, the fastidious aerobes on horse blood plates and the anaerobe on FAA plates. Throughout the study, the aerobes were cultured under aerobic conditions, the fastidious at 5% $CO_2$ and the anaerobe under strict anaerobic conditions at 37° C. At the time of testing, loopfuls of colonies selected from 18- to 24-hour agar plates for the aerobes and fastidious aerobes were suspended in 5 ml saline in 10 ml tubes containing 10 glass beads a 3 mm in diameter.

The anaerobes were suspended in Concept 400 and the diluent was reduced *Brucella* broth supplemented with hemin (5 µg/ml), vitamin K1 (1 µg/ml), and lysed horse blood (5%). The cell suspensions were then vortexed vigorously for 1 minute to obtain a turbid suspension. Each suspension of the aerobes and fastidious aerobes was adjusted to equal OD 0.28 at 475 nm using a spectrophotometer, which correlates approximately to $1-3 \times 10^8$ CFU/ml with most species. For the anaerobe, the OD measurement turned out to be difficult due to the use of blood in the culture medium. Hence, it was suspended to equal 0.5 Mc Farland standard and the cell density of the inoculum checked by plate count. The aerobes and fastidious aerobes were further diluted in saline 10 times so that the inoculum concentration equaled to $1.5-3.0 \times 10^7$ CFU/ml. The anaerobe was not diluted but used directly as is. The different aerobic and fastidious aerobic bacterial suspensions were transferred to respective wells of a 96 well plate. *A. baumannii, E. coli*, and *P. aeruginosa* were placed in one row, the Staphylococci spp. were placed in a second row, and the fastidious aerobes were placed in a third row of the plate. The anaerobe was transferred from a 25 ml multichannel pipette reservoir.

Microdilution Preparation and the MIC Test

The Microdilution Preparations and the MIC tests were performed as in example 13. MIC microdilution assays were run in triplicate to assess the MIC values for glucono-δ-lactone (GDA) (Table 10).

TABLE 10

Minimum inhibitory concentrations (MICs) for GDA against *Escherichia coli, Staphylococcus epidermidis, Staphylococcus aureus, Pseudomonas aeruginosa, Acetinobacter baumanii, Streptococcus pyogenes, Streptococcus agalactiae*, Beta-Hemolytic *Streptococci* Groups C and G and *Porphyromonas gingivalis*.

| Strain | CCUG identification | MIC (g/ml) |
|---|---|---|
| A. baumanni | CCUG 57035 | 0.0031 |
| E. coli | CCUG 3274 | 0.0063 |
| P. aeruginosa | CCUG 56489 | 0.0031 |
| S. aureus | CCUG 15915 | 0.0063 |
| S. epidermis | CCUG 23118 | 0.0031 |
| S. agalactiae | CCUG 29376 | 0.0031 |
| Beta-Hemolytic Streptococci Group C | CCUG 4211 | 0.0016 |
| Beta-Hemolytic Streptococci Group G | CCUG7975 | 0.0031 |
| S. pyogenes | CCUG 47803 | 0.0031 |
| P. gingivalis | CCUG 25893 | 0.0031 |

The minimum inhibitory concentration (MIC) value of GDA against *Escherichia coli, Staphylococcus epidermidis, Staphylococcus aureus, Pseudomonas aeruginosa, Acetinobacter baumanii, Streptococcus pyogenes, Streptococcus agalactiae*, Beta-Hemolytic Streptococci Groups C and G and *Porphyromonas gingivalis* is generally lower than the MIC value of GDA against *Lactobacillus iners* and *Lactobacillus crispatus* (Example 13). Thus, GDA is more efficient against the these pathogens than against the benign *Lactobacillus iners* and *Lactobacillus* crispatus.

The invention claimed is:

1. A method for preventing preterm birth in a pregnant individual with bacterial vaginosis, said method consisting of administering to said individual a pharmaceutical composition comprising a compound of Formula XX,

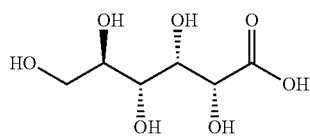

XX or a lactone thereof of formula XIX or XXI,

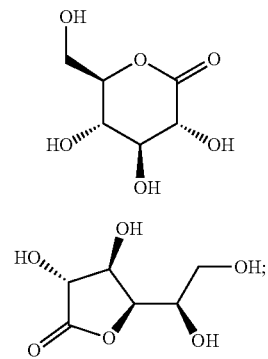

XIX

XXI and
preventing said preterm birth by said administration;
wherein said pharmaceutical composition comprises at least 5 wt % of the compound of Formula XX, XIX, XXI or combination thereof, and wherein said compound of Formula XX, XIX, XXI or combination thereof are the sole antimicrobial agent in said pharmaceutical composition.

2. The method according to claim 1, wherein the compound is of Formula XIX or Formula XX.

3. The method according to claim 1, wherein the compound is of Formula XIX.

4. The method according to claim 1, wherein the pharmaceutical composition comprises the compound of Formula XIX and the compound of Formula XX.

5. The method according to claim 1, wherein the pharmaceutical composition comprises no more than 10 wt % water.

6. The method according to claim 1, wherein the pharmaceutical composition consists of the compound of Formula XIX alone or in combination with the compound of Formula XX or the compound of Formula XXI, or both, and one or more pharmaceutically acceptable excipients.

7. The method according to claim 1, wherein the individual is a mammal.

8. The method according to claim 7, wherein the mammal is a human.

9. The method of claim 1, wherein said individual has an elevated risk for preterm birth.

10. The method according to claim 1, wherein the pharmaceutical composition is administered vaginally.

11. The method according to claim 1, wherein said pharmaceutical composition is formulated as a tampon, vagitorium, vaginal aerosol, vaginal cup, vaginal gel, vaginal insert, vaginal patch, vaginal ring, vaginal sponge, vaginal suppository, vaginal cream, vaginal emulsion, vaginal foam, vaginal lotion, vaginal ointment, vaginal powder, vaginal shampoo, vaginal solution, vaginal spray, vaginal suspension, vaginal tablet, vaginal rod, vaginal disc, vaginal device, and any combination thereof, or wherein the pharmaceutical composition is present on a sanitary napkin, an incontinence pad or diaper, or a panty liner.

12. The method according to claim 1, wherein said compound is administered as an oligomer or polymer.

13. The method according to claim 12, wherein the oligomer or polymer comprises one or more compounds selected from the group consisting of gluconic acid and δ-gluconolactone.

* * * * *